(12) United States Patent
Bowden

(10) Patent No.: US 6,792,947 B1
(45) Date of Patent: Sep. 21, 2004

(54) FLOW CONTROL VALVE FOR MANUAL RESUSCITATOR DEVICES

(75) Inventor: Kevin D. J. Bowden, Orangeville (CA)

(73) Assignee: O-Two Systems International Inc. (CA)

( * ) Notice: Subject to any disclaimer, the term of this patent is extended or adjusted under 35 U.S.C. 154(b) by 386 days.

(21) Appl. No.: 09/648,143

(22) Filed: Aug. 25, 2000

(51) Int. Cl.$^7$ ............................ A62B 7/00; A61M 16/00

(52) U.S. Cl. ............................ 128/205.17; 128/203.11; 128/205.14; 128/205.13; 128/203.28; 128/207.14; 128/207.16; 137/908

(58) Field of Search ........................ 128/203.11, 204.25, 128/205.17, 205.14, 205.13, 204.18, 203.28, 202.28, 202.29, 207.16, 207.14, 204.28; 137/908, 102, 107, 1

(56) References Cited

U.S. PATENT DOCUMENTS

| | | | | |
|---|---|---|---|---|
| 2,990,838 A | * | 7/1961 | Cross ........................ | 137/102 |
| 3,009,459 A | * | 11/1961 | Ruben ..................... | 128/205.13 |
| 3,610,237 A | * | 10/1971 | Barkalow et al. ....... | 128/204.19 |
| 3,672,366 A | * | 6/1972 | Burchell et al. ........ | 128/205.24 |
| 3,964,476 A | * | 6/1976 | Palleni ................... | 128/205.13 |
| 4,004,603 A | * | 1/1977 | Jones ....................... | 137/107 |
| 4,192,301 A | | 3/1980 | Hardwick ............... | 128/205.17 |
| 4,239,038 A | * | 12/1980 | Holmes .................. | 128/205.13 |
| 4,622,964 A | * | 11/1986 | Flynn ...................... | 128/205.24 |
| 4,774,941 A | * | 10/1988 | Cook ....................... | 128/205.13 |
| 4,821,713 A | * | 4/1989 | Bauman .................. | 128/205.13 |
| 4,836,198 A | * | 6/1989 | Gates ...................... | 128/205.18 |
| 4,898,167 A | | 2/1990 | Pierce et al. ............ | 128/205.16 |
| 5,140,982 A | | 8/1992 | Bauman .................. | 128/205.13 |
| 5,230,330 A | * | 7/1993 | Price ....................... | 128/203.11 |
| 5,301,667 A | | 4/1994 | McGrail et al. ........ | 128/205.14 |
| 5,368,022 A | | 11/1994 | Wagner ................... | 128/205.24 |
| 5,398,714 A | * | 3/1995 | Price ....................... | 137/102 |
| 5,425,358 A | | 6/1995 | McGrail et al. ........ | 128/205.24 |
| 5,492,115 A | * | 2/1996 | Abramov et al. ....... | 128/205.24 |
| 5,537,998 A | * | 7/1996 | Bauman .................. | 128/205.23 |
| 5,537,999 A | * | 7/1996 | Dearman et al. ....... | 128/205.25 |
| 5,557,049 A | | 9/1996 | Ratner .................... | 73/715 |
| 5,619,988 A | | 4/1997 | Mattila et al. .......... | 128/205.24 |
| 5,632,298 A | * | 5/1997 | Artinian ................. | 137/102 |
| 5,651,361 A | * | 7/1997 | Dearman et al. ....... | 128/205.25 |
| 5,687,709 A | * | 11/1997 | Akerberg ................ | 128/203.12 |
| 5,722,394 A | | 3/1998 | Loescher ................ | 128/205.24 |
| 5,727,546 A | | 3/1998 | Clarke et al. ........... | 128/203.15 |
| 5,878,743 A | | 3/1999 | Zdrojkowski et al. . | 128/204.23 |
| 5,944,013 A | | 8/1999 | Burch ..................... | 128/205.14 |
| 6,102,038 A | * | 8/2000 | DeVries .................. | 128/205.24 |
| 6,516,800 B1 | * | 2/2003 | Bowden .................. | 128/204.18 |
| 6,622,743 B1 | * | 9/2003 | Kohn et al. ............. | 137/1 |

OTHER PUBLICATIONS

A.H.A., *Guidelines for Cardiopulmonary Resuscitation and Emergency Cardiac Care*—J.A.M.A., Oct. 28, 1999, 2171–2295.

(List continued on next page.)

*Primary Examiner*—Henry Bennett
*Assistant Examiner*—Mital Patel
(74) *Attorney, Agent, or Firm*—Kusner & Jaffe

(57) ABSTRACT

An improved manual resuscitation device such as a bag-valve-mask (BVM) device with flow control valve to eliminate the danger of patient distension and aspiration of stomach contents during ventilation. The BVM having the usual patient mask with a gas inlet and flexible patient face sealing edge, flexible manually squeezed bag with a one way intake and output valves in flow communication with a gas source and the mask inlet, and exhaust port for exhausting exhaled gas from the mask when the bag output valve is closed. The flow control valve is interposed between the mask and bag to automatically and variably limit the rate of gas flow from the bag to the mask between a predetermined minimum flow rate and a maximum flow rate. A similar flow control valve can be included in any manual resuscitation device such as a pocket mask or face shield to equal advantage.

10 Claims, 3 Drawing Sheets

OTHER PUBLICATIONS

Cummins, R.O. et al., *Ventilation Skills of Emergency Medical Technicians: A Teaching Challenge for Emergency Medicine*, Ann. Emerg. Med., Oct. 1986; 15:1187–1192.

Stone, B.J. et al., *The Incidence of Regurgitation During Cardipulmonary Resuscitation: A Comparison Between the Bag Valve Mask and Laryngeal Mask Airway*, Resuscitation 38 (1998), 3–6.

Elling, B. A. et al., *An Evaluation of Emergency Medical Technician's Ability to Use Manual Ventilation Devices*, Ann. Emerg. Med., Dec. 1983, 12:765–768.

Rhee, K.J. et al., *Field Airway Management of the Trauma Patient, The Efficacy of Bag Mask Ventilation*, Am. J. Emerg. Med., 1988, 6:333–336.

Manoranian, C.S. et al., *Bag–Valve–Mask Ventilation; Two Rescuers Are Better Than One: Preliminary Report*, Critical Care Medicine, 1985, 13:122–123.

Lande, S. et al., *Comparing Ventilatory Techniques During CPR*, J.E.M.S., May 1982.

Harrison, R.R. et al., *Mouth–to–Mouth Ventilation: A Superior Method of Rescue Breathing*, Ann. Emerg. Med., Feb. 1982, 11:74–76.

\* cited by examiner

FLOW CONTROL VALVE FOR MANUAL RESUSCITATOR DEVICES

TECHNICAL FIELD

The invention relates to a flow control valve for preventing gastric distention and aspiration of stomach contents due to excessive gas flow rates delivered to patients by controlling the flow rate of pressurized air from a manually operated resuscitation device, such as a Bag-Valve-Mask device, pocket mask, face shield, or endotracheal tube.

BACKGROUND OF THE ART

In the relevant art of pulmonary resuscitation using manually operated resuscitation devices, the Bag-Valve-Mask resuscitator (commonly referred to as a "BMV") has been the primary method of ventilating the patient in respiratory arrest for some 40 years. The BVM device is well known to those in the relevant art and examples of BVM designs are shown in U.S. Pat. Nos. 4,532,923 and 4,622,964 to Flynn. Cardio-pulmonary resuscitation (CPR) can be administered mouth-to-mouth without protection but recently to protect the patient and emergency medical personnel, use of various protective manually operated devices is common. For example, one way valves, patient exhalation valves and fabric shields are fitted to pocket masks and face shields in order to inhibit cross-contamination.

The clinical application of manually operated resuscitation devices including BVM devices, pocket masks, and face shields however is not based on scientific fact but rather on historical usage and the lack of an inexpensive alternative. Potentially dangerous excessive gas flow rates and pressure delivered to the patient have been documented using mechanical BVM's as well as the exhaled breath from the operator using pocket masks and face shields. The skill and training of the operator alone determines the efficacy of resuscitation when manually operated devices are used.

Clinical evidence that supports the use of BVMs is rare, whereas there is an abundance of evidence that clearly identifies BVMs as generally ineffective in providing adequate ventilations to the patient [for example, *A. H. A. Guidelines for Cardiopulmonary Resuscitation and Emergency Cardiac Care*—J. A. M. A. Oct. 28, 1992:2171–2295].

The BVM consists of a self inflating balloon at one end having a one way intake valve that allows gas to be drawn into the balloon as the balloon recoils after it has been manually squeezed by the user. The intake valve self seals when the inflated bag is squeezed, and opens when the bag is permitted to recoil naturally. On the other end of the balloon, a one way output valve permits the gas to leave the bag when squeezed directing the flow of gas to the patient through a facemask, or other airway adjunct. The output valve opens when the inflated bag is squeezed, and self seals when the bag is permitted to recoil naturally. The output valve when sealed diverts the exhausted gas from the patient out through an expiratory port on the valve housing. As a result of cyclical manual squeezing and recoil of the balloon, gas is pumped through the balloon to the patient mask.

The original BVM was a development from the "Black Anaesthesia Bag" whereby the black bag was supported internally by a foam, self inflating balloon causing the bag to recoil to its original shape when the squeezed bag was permitted to recoil when released.

Many versions of the BVM have been developed all with the same negative feature, namely that the delivered flow, tidal volume, airway pressure and frequency are totally dependent upon the operator's skill and hand size. The inability to control the output from the BVM has been subject of many studies and has been well documented. Prior to creation of the present invention, this problem has not been overcome. [For example: Cummins R. O. et al, *Ventilation Skills of Emergency Medical Technicians: A Teaching Challenge for Emergency Medicine*, Ann. Emerg. Med, October 1986; 15:1187–1192; Stone B. J. et al, *The Incidence of Regurgitation During Cardiopulmonary Resuscitation: A Comparison Between the Bag Valve Mask and Laryngeal Mask Airway*, Resuscitation 38 (1998) 3–6; Elling, B. A. et al, *An Evaluation of Emergency Medical Technician's Ability to Use Manual Ventilation Devices*, Ann. Emerg. Med. 12:765–768, December 1983; Rhee, K. J. et al, *Field Airway Management of the Trauma Patient, The Efficacy of Bag Mask Ventilation*, Am. J. Emerg. Med. 1988;6:333–336; Manoranian, C. S. et al, *Bag-Valve-Mask Ventilation; Two Rescuers Are Better Than One: Preliminary Report*, Critical Care Medicine, 1985;13:122–123; Lande, S. et al, *Comparing Ventilatory Techniques During CPR*, J. E. M. S. May 1982; Harrison, R. R. et al, *Mouth-to-Mouth Ventilaion: A Superior Method of Rescue Breathing*, Ann. Emerg. Med., 11:74–76, February 1982].

Additionally, the requirements of ventilation have changed in recent years causing more concern over the use of the BVM and the volume, frequency of ventilation, airway pressures and flows that the average skilled operator can deliver. A number of the above clinical papers have documented this inability by even highly skilled operators to consistently deliver correct volumes and ventilation rates without causing problems for the patient including gastric distention and aspiration of stomach contents leading to patient morbidity and even death. Not only BVM's result in unsatisfactory ventilation but any manually operated resuscitation device including pocket masks and face shield yields similar results due to the reliance on the skill and training of the operator.

The quality of ventilation delivery when operator powered devices are used is particularly unpredictable and varies greatly according to experience, training and general coordination ability. To provide adequate ventilation, the emergency medical technician should pay attention to consistently timed tidal volumes of approximately equal volume and pressure dependant on the body size and age of the patient. However emergency care personnel are often under extreme stress and have many other duties to perform in urgent care situations that tend to reduce the attention and level of care directed to ventilation techniques.

While normal breathing requires muscle action (diaphragm, intercostals and others) to produce a negative pressure (subatmospheric or vacuum) within the chest to draw air into the lungs, artificial ventilation is accomplished by forcing air or oxygen into the lungs under an external positive pressure.

The positive pressure required to deliver a set volume (tidal volume) of gas to a patient is dependent on two factors: (1) the compliance, stiffness or elasticity of the lung, and (2) the resistance to gas flow within the conducting airways. For example, a "stiff" lung that is damaged by pulmonary fibrosis, disease or trauma requires a higher pressure to deliver a set tidal volume than a normal elastic lung. Similarly, gas will encounter less resistance through a normal airway that is not narrowed by bronchospasm or asthma, kinked by a poor airway opening technique, or plugged with blood, mucous, vomit or other debris.

As a result, manual and automatic ventilation techniques must accommodate a range of pressures. With a cormnon tidal volume of gas that is delivered, the patient's lung and airway condition will determine the pressure needed to ventilate the patient. However, there is a safe upper limit to the pressures that can be used to prevent lung damage. The danger of pneumothorax or lung rupture due to excessive pressures is considered to occur between 75 and 85 cmH$_2$O.

Regarding the peak flow rates required to adequately ventilate an adult in respiratory arrest a generally accepted rate is a tidal volume of one liter at 12 breath cycles per minute. The breathing rate of 12 breath cycles/minute equals 5 seconds/breath cycle (60/12). Assuming that it takes about one half the length of time to inhale as to exhale (1:2 IE Ratio), the inhale portion of the breathing cycle takes approximately 1.5 seconds/inhaled breath (5 seconds/3=1.67 or approx. 1.5). The ideal flow rate therefore is approximately 40 liters/minute derived by (1 liter per inhaled breath/1.5 seconds per inhaled breath)×60 seconds per minute=40 liters per minute.

Therefore the accepted limit of ideal flow rate is in the order of 40 liters per minute and limit of maximum pressure is approximately 75 and 85 cmRH$_2$O. Tests conducted however indicate that excessive peak flows of 200 liters/minute at pressures of 100 cmH$_2$O are commonly delivered when fully trained emergency medical personnel use the manual ventilating techniques involving Bag-Valve-Masks and mouth-to-mouth resuscitation, with patient isolating valves on pocket masks and face shields.

The problem in the emergency medical service field is that users generally perceive that they are competent in using the manual devices and that the manual devices and methods themselves are efficacious. Many technicians claim that the manual "feel" of the BVM allows them to make clinical judgements on the patient's lung condition. In reality what they are feeling is the backpressure created by the high flow rates generated when squeezing the bag too hard or for too short an inspiratory time. The backpressure condition masks the actual compliance and resistance of the patient's airway.

Judging from the clinical research, noted above, these beliefs are totally unfounded. Ideally, an automatic ventilator with appropriate patient condition monitoring circuits and cautionary alarms can be used to provide consistent care to the patient. However, due to the perceived high cost, many decision-makers are not persuaded to spend the extra funds on automatic devices since they perceive that the manually operated devices function efficiently. Such short term thinking does not consider the true cost of disposable BVMs, pocket masks and face shields including the risk to a patient's health by depending entirely on the skill and attention of an operator.

The prior art has proposed solutions that do not control the gas flow, but provide high pressure relief exhaust ports or an indication of the gas pressure within a BVM circuit. The prior art does not appear to recognize that excessive pressure and flow rates can be delivered from pocket masks and face shields as well.

For example, U.S. Pat. No. 5,557,049 to Ratner discloses a disposable manometer, which is used on a BVM device to indicate the pressure of gas being delivered to the patient. The Ratner solution presumes that the user has time and attention available to view the manometer and adjust their ventilation efforts accordingly. However, in reality during literally life and death situations the operators are constantly preoccupied. The bag-valve-mask requires almost continuous contact with one hand of the user and thereby imposes extreme limitations on their actions. In an effort to accomplish more than one task at a time, the operator can easily neglect the bag-valve-mask or deliver inconsistent ventilation to the patient.

U.S. Pat. No. 5,722,394 to Loescher shows an example of a BVM including a high pressure exhaust valve. U.S. Pat. No. 5,537,998 to Bauman provides a spring loaded piston which serves to detect and exhaust excess air pressure in a simple manual resuscitator with vent ports open depending on the extent of internal pressure delivered to the patient with the manual resuscitator.

None of the prior art devices specifically prevent stomach aspiration and distention by controlling the flow rate, pressure or volume of gas with any degree of accuracy.

It is an object of the present invention to control the flow of gas during respiratory resuscitation thereby limiting the gas flow between a minimum and maximum being manually delivered by the operator.

It is a further object of the invention to provide control of gas flow by modifying the established disposable BVM, pocket mask or face shield to ensure acceptance with minimal increase in price.

Further objects of the invention will be apparent from review of the disclosure and description of the invention below.

DISCLOSURE OF THE INVENTION

The invention relates to an improved bag-valve-mask (BVM) device with flow control valve to eliminate the danger of patient distension and aspiration of stomach contents during ventilation. The BVM having the usual patient mask with a gas inlet and flexible patient face sealing edge, flexible manually squeezed bag with a one way intake and output valves in flow communication with a gas source and the mask inlet, and exhaust port for exhausting exhaled gas from the mask when the bag output valve is closed. The flow control valve is interposed between the mask and bag to automatically and variably limit the rate of gas flow from the bag to the mask between a predetermined minimum flow rate and a maximum flow rate.

Further details of the invention and its advantages will be apparent from the detailed description and drawings included below.

BRIEF DESCRIPTION OF THE DRAWINGS

In order that the invention may be readily understood, one preferred embodiment of the invention will be described by way of example, with reference to the accompanying drawing wherein.

Further details of the invention will become apparent from the detailed description presented below.

DETAILED DESCRIPTION OF PREFERRED EMBODIMENTS

Figure 1:
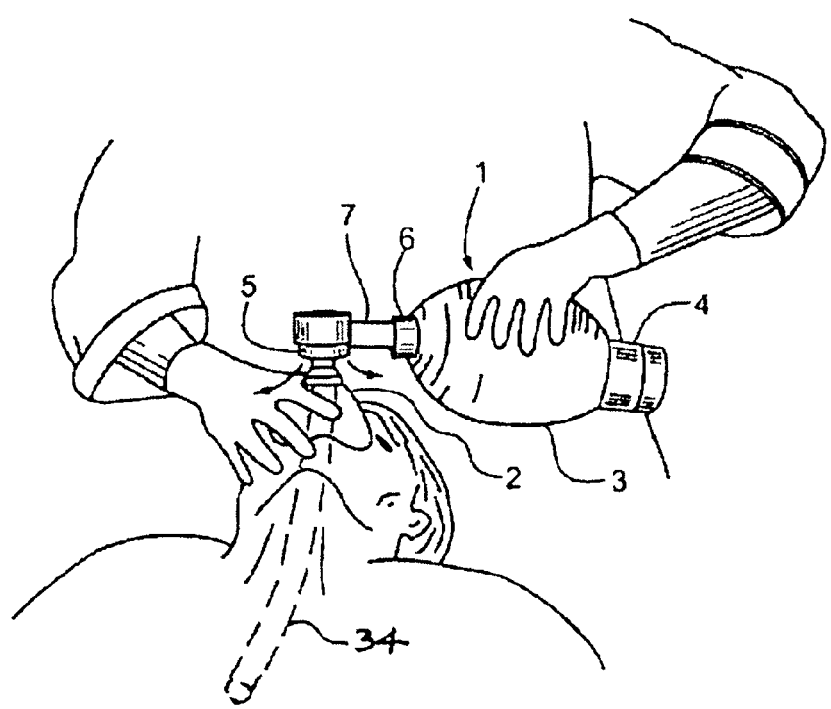
FIG. 1 is a view of a Bag-Valve-Mask where a patient ventilated by the operator and the gas flow is controlled with a flow control valve located in a modified neck bushing disposed between the bag and the mask, the flow control valve having a frusto-conical valve plug slidably biased to the right and moved to the left to restrict the gas flow through the valve in response to gas flow impinging on the upstream surface of the valve plug.
Figure 2:
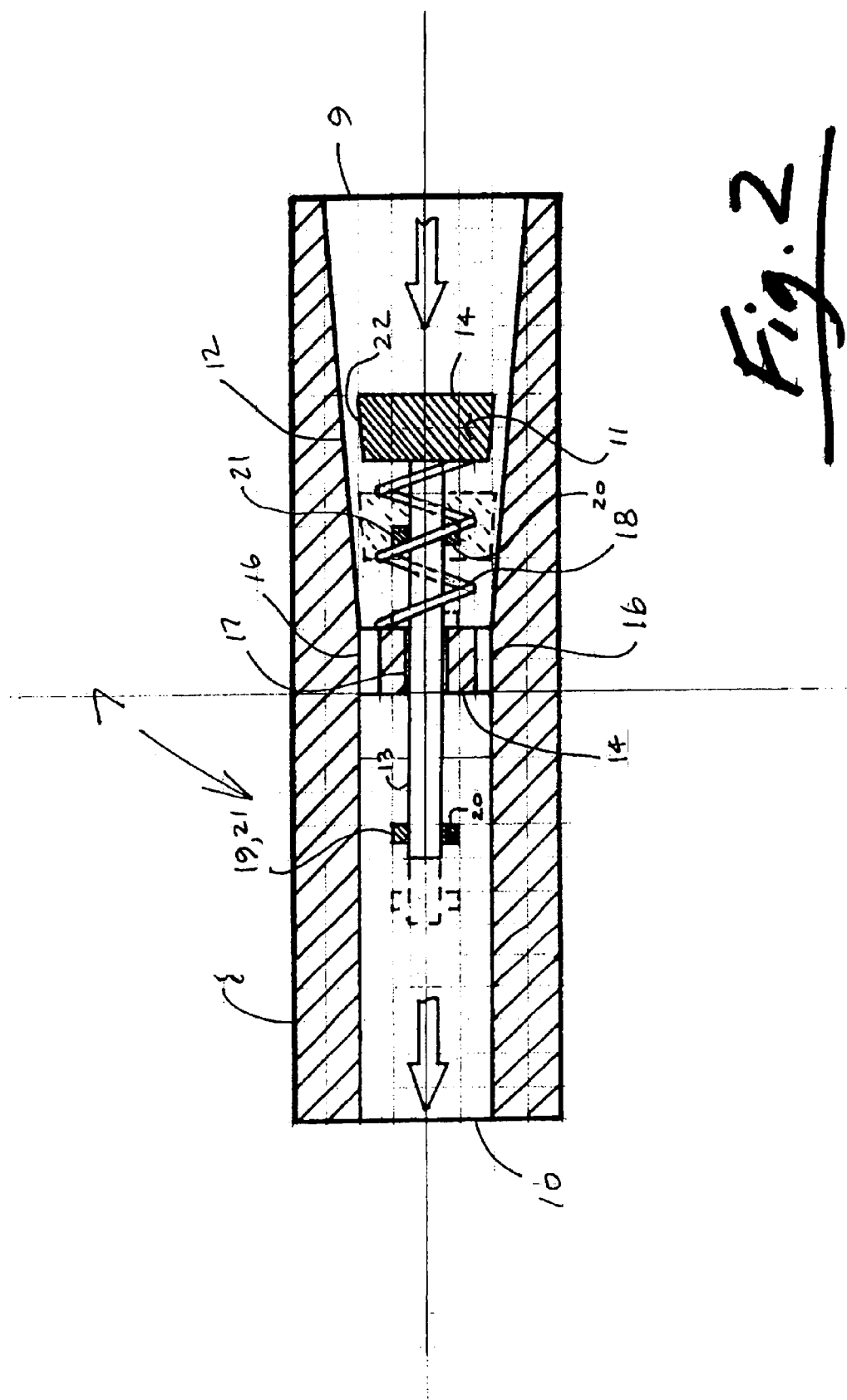
FIG. 2 is a longitudinal section view through the flow control valve with sliding valve stem, spring loaded frusto-conical piston and frusto-conical inlet chamber serving as a valve seat.

FIG. 1 shows the general arrangement and use of a bag-valve-mask device 1 also known as a BVM. The invention centres on a simple but valuable modification to the conventional BVM by insertion of a flow control valve 7 between the patient mask 2 and the bag 3. Details of one embodiment of flow control valve 7 are shown in FIG. 2.

Figure 3:
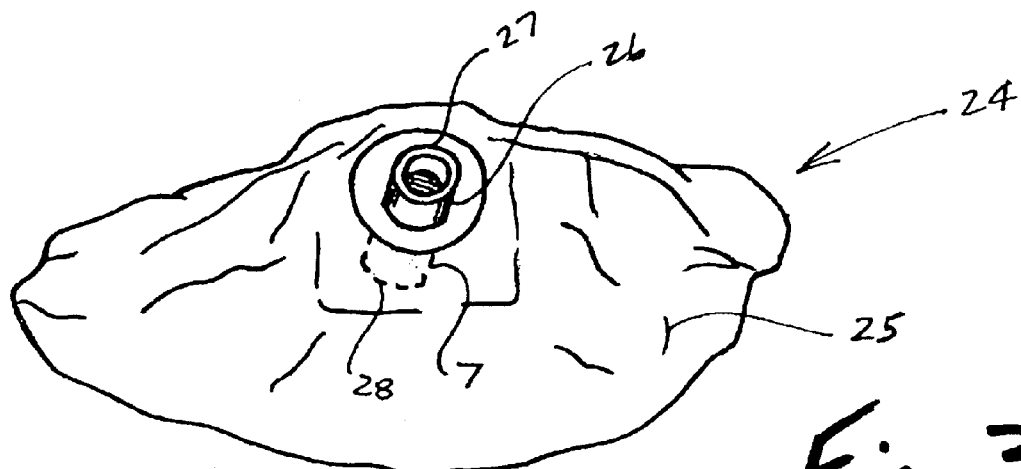
FIG. 3 is a perspective view of a face shield with a flow control valve in accordance with a second embodiment of the invention disposed within the tube extending through the plastic sheet.
Figure 4:
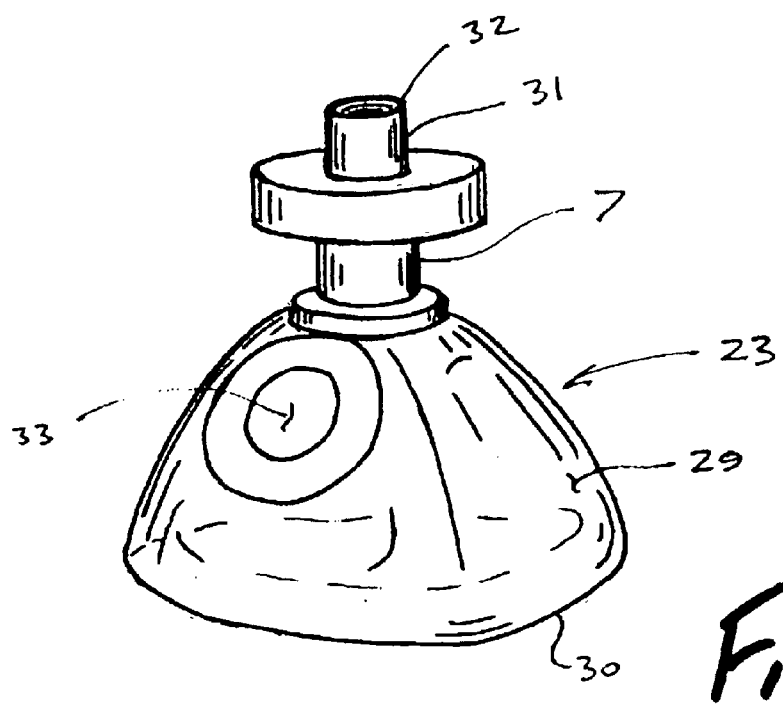
FIG. 4 is a perspective view of a face shield with a flow control valve in accordance with a third embodiment of the invention disposed within the tube extending through top of the patient mask.

A similar flow control valve 7 can be included in any manual resuscitation device such as a pocket mask 23 as indicated in FIG. 4 or face shield 24 as indicated in FIG. 3 to equal advantage.

In the first embodiment applied to a BVM device of FIG. 1, the patient mask 2 has a gas inlet and a patient face sealing edge held by the operator's hand. The operator's other hand cyclically squeezes and releases the flexible bag 3 to pump gas through a one way intake valve 4 from a breathable gas source, through a one way output valve 6 in flow communication with the mask 2. Exhaust ports 5 exhaust exhaled gas from the mask 2 when the bag output valve 6 is closed. If desired, the bag 3 may be used with an endotracheal tube 34, with or without the accompanying face mask 2, to deliver breathable gas directly to the patient's tracheal tubes and lungs where there is a blockage of the upper patient's airway caused by inflammation, injury or trauma.

The flow control valve 7 is disposed in flow communication between the mask 2 and bag 3 for automatically variably limiting the rate of gas flow from the bag 3 to the mask 2 between a predetermined minimum flow rate and a maximum flow rate. The tidal volume delivered will remain relatively constant since the bag 3 contains a limited volume of gas and the operator should generally squeeze the bag 3 until the bag 3 is deflated to the same degree for each breath. The flow control valve 7 controls the rate or speed (for example in units of liters per minute) of delivering the tidal volume to reduce the variation in flow rate when used by different operators, with different size hands, varying strength, varying skill etc.

As shown in FIG. 2, the flow control valve 7 includes a housing 8 with control valve inlet 9, control valve outlet 10 and an orifice 12 therebetween. Gas flow sensor surface 14 senses the impingement of gas flowing from with the valve inlet 9 and the resultant sliding of the valve plug 11 against the bias of spring 18 serves to automatically restrict gas flow through the orifice 12 in response to the flow of gas impinging on the impingement surface 14 of the plug 11. Other devices to sense the gas flow besides a spring loaded valve plug 11 can be provided but at higher cost than the simple device illustrated such as: a flexible diaphragm; pneumatic pressure sensing valves; rotating flow meter propellers; and electrical gas flow sensors, that can measure the gas flow and then mechanically, pneumatically or electrically operate a separate flow control valve. The embodiment illustrated in the accompanying drawings uses the upstream surface 14 of the valve plug 11 to sense the incoming air flow, which applies a drag force against the plug 11 and spring 18 to move the plug 11 and thus automatically restrict the orifice 12. This combined sensing and valve operating mechanism is very simple and low cost compared to a separate sensor and valve arrangement.

As shown in FIG. 2 a simple reliable and inexpensive means to automatically variably restrict the orifice 12 can be constructed using a conical valve seat 12 and movable conical valve plug 11 with a gas flow impingement surface 14 and a valve seat mating surface 22. The plug 11 is normally biased away from the valve seat 12 by the spring 18 and is urged toward the valve seat 12 by the force exerted by gas flow against the flow impingement surface 14.

To mount the plug 11 within the housing 8 a bulkhead 14 is included downstream of the valve seat 12. The bulkhead 14 includes perforations 16 that can be sized to ensure that at all times a minimum gas flow is permitted to pass through the valve 7 when the plug 11 is moved to it's highest point. The spring and motion limiter 21 serve to prevent complete closure of the gas flow control valve and always permit a minimum gas flow to pass through.

The plug 11 is mounted to an upstream end of a valve stem 13 and the valve stem 13 is slidably mounted within a through bore 17 in the bulkhead 14 with the spring 18 disposed about the valve stem 13 between the plug 14 and bulkhead 14. The valve stem 13 preferably includes a retainer 19 downstream of the bulkhead 14 for preventing removal of the stem 13 from the bore 17. The retainer 19 has a bulkhead abutting surface 20, as does the motion limiter 21. Both surfaces 20 are disposed on the valve stem 13 a selected distance from the bulkhead 14 for limiting the range that the stem 13 can slide within the bore 17. The valve stem 13 and bulkhead bore 17 preferably have a clearance space disposed therebetween sufficient to allow lateral motion of the valve plug 11 relative to the valve seat 12. Such clearance not only ensures that the stem 13 will not unintentionally bind but also allows the plug 11 to be self-centering and prevent binding of the valve seat 12 and plug surface 22.

With regard to the second embodiment shown in FIG. 2, the same flow control valve 7 is adapted to use with a face shield 24. The face shield 24 has a flexible plastic sheet 25 with a tube 26 therethrough. The tube 26 has an upper end with an operator mouthpiece 27 about the gas inlet where the operator breathes exhaled air to the patient. The lower end has a patient mouthpiece 28 which is inserted into the patient's mouth and the sheet 25 serves to protect against contamination. Since conventional face shields include a tube 26 usually with a one-way intake valve (not shown) and patient exhalation valve (not shown), the invention may be easily adopted for use with a face shield 24 by including the flow control valve 7 housed within the tube 26.

With regard to the third embodiment shown in FIG. 3, the same flow control valve 7 is adapted to use with a pocket mask 23. The pocket mask 24 has a flexible patient mask 29, with a patient sealing edge 30, and a tube 31 that has an upper end with an operator mouthpiece 32 about the gas inlet where the operator breathes exhaled air to the patient. The lower end of the tube 31 is sealed to the mask 29 which serves to protect against contamination and gas pressure loss. Since conventional pocket masks include a tube 31 usually with a one-way intake valve (not shown) and patient exhalation valve 33, the invention may be easily adopted for use with a pocket mask 23 by including the flow control valve 7 housed within the tube 31.

Further embodiments include using the flow control valve 7 with a manually ventilated endotracheal tube 34 that is inserted directly into the patient's trachea and includes protruding end into which the operator attaches a bag-valve-mask device 1 to ventilate the patient, as shown in FIG. 1. The use of any manually operated ventilation device can be improved by controlling the gas flow rate with a flow control valve as described herein.

Although the above description and accompanying drawings relate to a specific preferred embodiment as presently contemplated by the inventor, it will be understood that the invention in its broad aspect includes mechanical and functional equivalents of the elements described and illustrated.

The embodiments of the invention in which an exclusive property or privilege is claimed are defined as follows:

1. A manually operated resuscitation device comprising:

a patient interface having a gas inlet and gas outlet adapted to deliver gas to a patient airway, the interface having a one way intake valve downstream of the gas inlet; and flow rate control valve, housed within a gas containment housing disposed in one-way flow communication between the patient interface gas inlet and a source of breathable gas, the flow rate control valve being operable between a minimum gas flow rate and a maximum gas flow rate conducting gas flow at a controlled rate in one direction through the housing from the source of breathable gas to the gas inlet of the patient interface, the flow rate control valve comprising a valve seat and a valve plug defining a flow rate control orifice between the valve seat and the valve plug, wherein the plug includes a gas flow impingement surface and a valve seat mating surface, the plug being normally biased away from the valve seat and urged toward the valve seat by gas flow impinging against the gas flow impingement surface.

2. A manually operated resuscitation device according to claim 1 wherein the patient interface is selected from the group consisting of: a bag-valve-mask device; a pocket mask device wherein the patient interface comprises a patient mask with said gas inlet and a patient face sealing edge; an endotracheal tube; and a face shield device comprising a flexible sheet with a tube therethrough, the tube having an upper end with operator mouthpiece about said gas inlet and a lower end with patient mouthpiece.

3. A manually operated resuscitation device according to claim 2 wherein said bag-valve-mask device comprises:

a patient mask having a patient face sealing edge;

a flexible bag having a one way intake valve in flow communication with said gas source and a one way output valve in flow communication with the mask inlet;

exhaust port valve in flow communication with the patient mask operable between a closed position and an open position wherein exhaled gas is exhausted from the mask when the one way output valve is closed.

4. A manually operated resuscitation device according to claim 1 wherein the housing includes a bulkhead downstream of the valve seat, the bulkhead including at least one perforation; and wherein the plug is mounted to an upstream end of a valve stem, the valve stem is slidably mounted within a through bore in the bulkhead with a spring disposed about the valve stem between the plug and bulkhead.

5. A manually operated resuscitation device according to claim 4 wherein the valve stem includes a retainer downstream of the bulkhead.

6. A manually operated resuscitation device according to claim 5 wherein the retainer comprises a shoulder with bulkhead abutting surface.

7. A manually operated resuscitation device according to claim 4 wherein the valve stem includes a motion limiter disposed on the valve stem a selected distance from the bulkhead.

8. A manually operated resuscitation device according to claim 7 wherein the motion limiter comprises a shoulder with bulkhead abutting surface.

9. A manually operated resuscitation device according to claim 4 wherein valve stem and bulkhead bore have a clearance space disposed therebetween sufficient to allow lateral motion of the valve plug relative to the valve seat.

10. A manually operated resuscitation device according to claim 1 wherein the valve seat and valve seat mating surface are conical surfaces.

* * * * *

UNITED STATES PATENT AND TRADEMARK OFFICE
CERTIFICATE OF CORRECTION

PATENT NO.        : 6,792,947 B1
APPLICATION NO. : 09/648143
DATED              : September 21, 2004
INVENTOR(S)       : Bowden It is certified that error appears in the above-identified patent and that said Letters Patent is hereby corrected as shown below:

The title page, showing an illustrative figure, should be deleted and substitute therefor the attached title page.

Delete drawing sheets 1-3, and substitute therefor the drawing sheets, consisting of FIGS. 1-4 as shown on the attached pages.

Signed and Sealed this

Twenty-eighth Day of July, 2009

JOHN DOLL
*Acting Director of the United States Patent and Trademark Office*

(12) United States Patent  (10) Patent No.: US 6,792,947 B1
Bowden  (45) Date of Patent: Sep. 21, 2004

(54) FLOW CONTROL VALVE FOR MANUAL RESUSCITATOR DEVICES

(75) Inventor: Kevin D. J. Bowden, Orangeville (CA)

(73) Assignee: O-Two Systems International Inc. (CA)

(*) Notice: Subject to any disclaimer, the term of this patent is extended or adjusted under 35 U.S.C. 154(b) by 386 days.

(21) Appl. No.: 09/648,143

(22) Filed: Aug. 25, 2000

(51) Int. Cl.[7] .......................... A62B 7/00; A61M 16/00

(52) U.S. Cl. ........................ 128/205.17; 128/203.11; 128/205.14; 128/205.13; 128/203.28; 128/207.14; 128/207.16; 137/908

(58) Field of Search ................ 128/203.11, 204.25, 128/205.17, 205.14, 205.13, 204.18, 203.28, 202.28, 202.29, 207.16, 207.14, 204.28; 137/908, 102, 107, 1

(56) References Cited

U.S. PATENT DOCUMENTS

| 2,990,838 | A | * | 7/1961 | Cross | 137/102 |
|---|---|---|---|---|---|
| 3,009,459 | A | * | 11/1961 | Ruben | 128/205.13 |
| 3,610,237 | A | * | 10/1971 | Barkalow et al. | 128/204.19 |
| 3,672,366 | A | * | 6/1972 | Burchell et al. | 128/205.24 |
| 3,964,476 | A | * | 6/1976 | Palleni | 128/205.13 |
| 4,004,603 | A | * | 1/1977 | Jones | 137/107 |
| 4,192,301 | A |  | 3/1980 | Hardwick | 128/205.17 |
| 4,239,038 | A | * | 12/1980 | Holmes | 128/205.13 |
| 4,622,964 | A | * | 11/1986 | Flynn | 128/205.24 |
| 4,774,941 | A | * | 10/1988 | Cook | 128/205.13 |
| 4,821,713 | A | * | 4/1989 | Bauman | 128/205.13 |
| 4,836,198 | A | * | 6/1989 | Gates | 128/205.18 |
| 4,898,167 | A |  | 2/1990 | Pierce et al. | 128/205.16 |
| 5,140,982 | A |  | 8/1992 | Bauman | 128/205.13 |
| 5,230,330 | A | * | 7/1993 | Price | 128/203.11 |
| 5,301,667 | A |  | 4/1994 | McGrail et al. | 128/205.14 |
| 5,368,022 | A |  | 11/1994 | Wagner | 128/205.24 |
| 5,398,714 | A | * | 3/1995 | Price | 137/102 |
| 5,425,358 | A |  | 6/1995 | McGrail et al. | 128/205.24 |
| 5,492,115 | A | * | 2/1996 | Abramov et al. | 128/205.24 |
| 5,537,998 | A | * | 7/1996 | Bauman | 128/205.23 |
| 5,537,999 | A | * | 7/1996 | Dearman et al. | 128/205.25 |
| 5,557,049 | A |  | 9/1996 | Ratner | 73/715 |
| 5,619,988 | A |  | 4/1997 | Mattila et al. | 128/205.24 |
| 5,632,298 | A | * | 5/1997 | Artinian | 137/102 |
| 5,651,361 | A | * | 7/1997 | Dearman et al. | 128/205.25 |
| 5,687,709 | A | * | 11/1997 | Akerberg | 128/203.12 |
| 5,722,394 | A |  | 3/1998 | Loescher | 128/205.24 |
| 5,727,546 | A |  | 3/1998 | Clarke et al. | 128/203.15 |
| 5,878,743 | A |  | 3/1999 | Zdrojkowski et al. | 128/204.23 |
| 5,944,013 | A |  | 8/1999 | Burch | 128/205.14 |
| 6,102,038 | A | * | 8/2000 | DeVries | 128/205.24 |
| 6,516,800 | B1 | * | 2/2003 | Bowden | 128/204.18 |
| 6,622,743 | B1 | * | 9/2003 | Kohn et al. | 137/1 |

OTHER PUBLICATIONS

A.H.A., *Guidelines for Cardiopulmonary Resuscitation and Emergency Cardiac Care*—J.A.M.A., Oct. 28, 1999, 2171–2295.

(List continued on next page.)

*Primary Examiner*—Henry Bennett
*Assistant Examiner*—Mital Patel
(74) *Attorney, Agent, or Firm*—Kusner & Jaffe

(57) ABSTRACT

An improved manual resuscitation device such as a bag-valve-mask (BVM) device with flow control valve to eliminate the danger of patient distension and aspiration of stomach contents during ventilation. The BVM having the usual patient mask with a gas inlet and flexible patient face sealing edge, flexible manually squeezed bag with a one way intake and output valves in flow communication with a gas source and the mask inlet, and exhaust port for exhausting exhaled gas from the mask when the bag output valve is closed. The flow control valve is interposed between the mask and bag to automatically and variably limit the rate of gas flow from the bag to the mask between a predetermined minimum flow rate and a maximum flow rate. A similar flow control valve can be included in any manual resuscitation device such as a pocket mask or face shield to equal advantage.

10 Claims, 3 Drawing Sheets

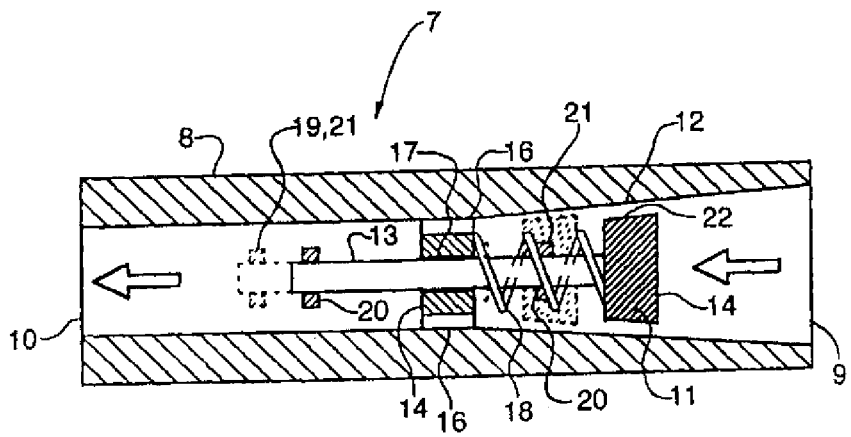

UNITED STATES PATENT AND TRADEMARK OFFICE
CERTIFICATE OF CORRECTION

PATENT NO.         : 6,792,947 B1
APPLICATION NO. : 09/648143
DATED              : September 21, 2004
INVENTOR(S)       : Bowden Page 3 of 5

It is certified that error appears in the above-identified patent and that said Letters Patent is hereby corrected as shown below:

Sheet 1, Figure 1

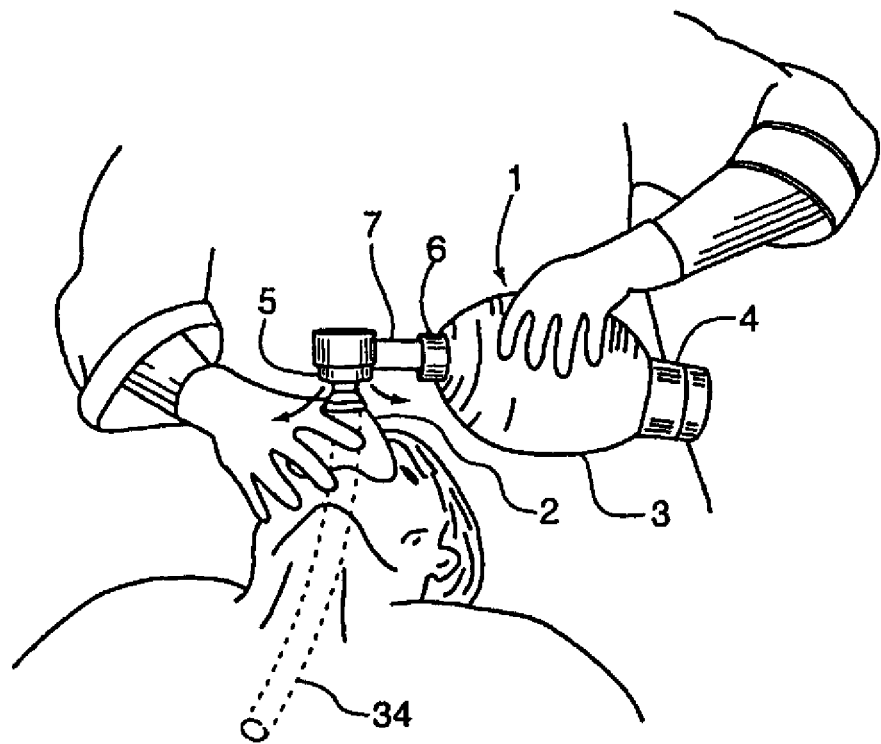

FIG.1

UNITED STATES PATENT AND TRADEMARK OFFICE
CERTIFICATE OF CORRECTION

PATENT NO. : 6,792,947 B1
APPLICATION NO. : 09/648143
DATED : September 21, 2004
INVENTOR(S) : Bowden It is certified that error appears in the above-identified patent and that said Letters Patent is hereby corrected as shown below:

Sheet 2, Figure 2

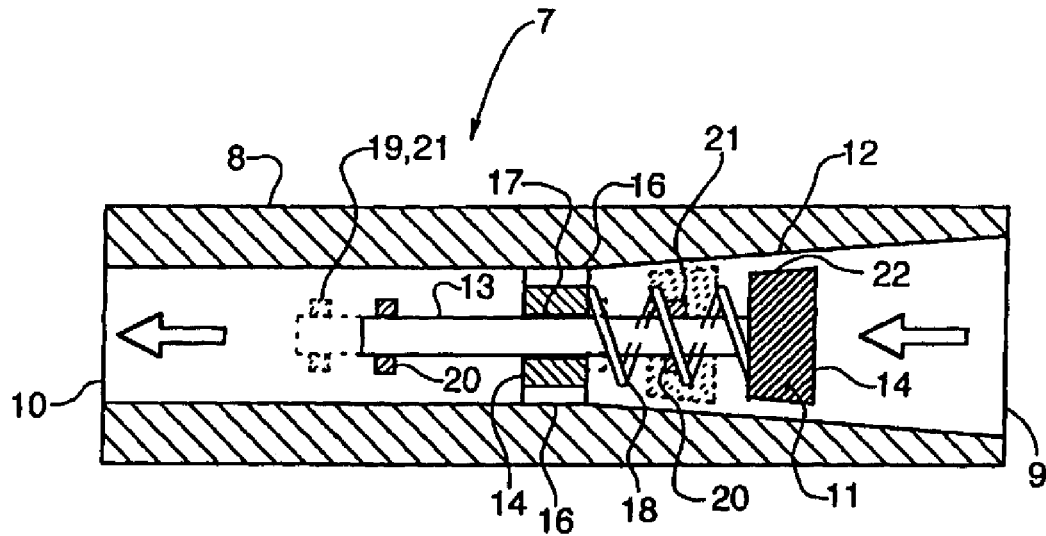

FIG.2

UNITED STATES PATENT AND TRADEMARK OFFICE
CERTIFICATE OF CORRECTION

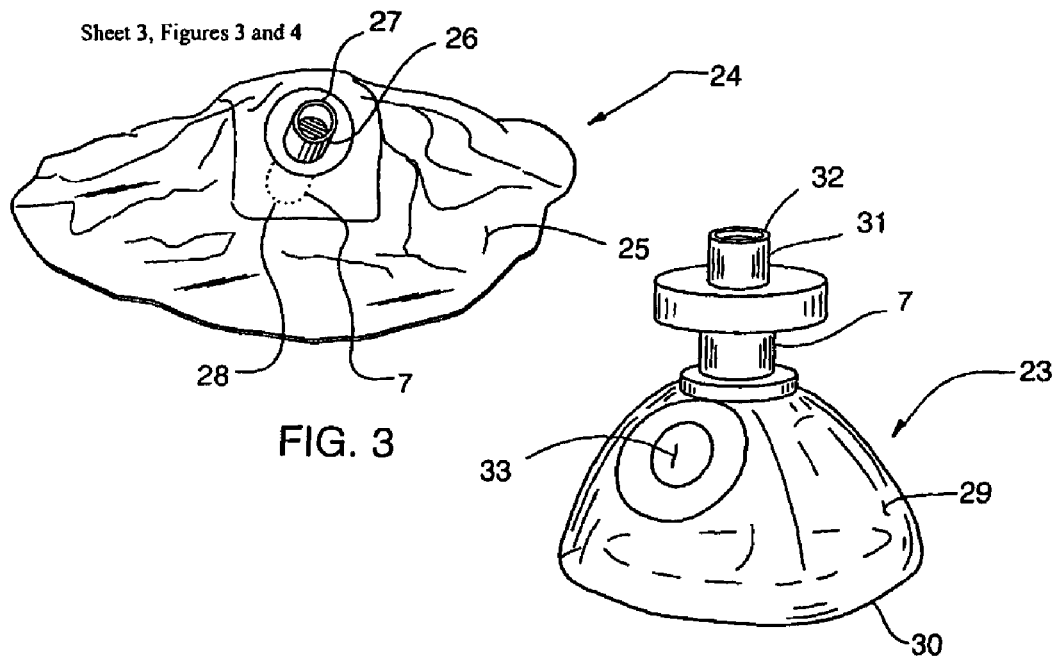

PATENT NO. : 6,792,947 B1 Page 5 of 5
APPLICATION NO. : 09/648143
DATED : September 21, 2004
INVENTOR(S) : Bowden It is certified that error appears in the above-identified patent and that said Letters Patent is hereby corrected as shown below: